United States Patent [19]

Huebner et al.

[11] Patent Number: 4,685,328

[45] Date of Patent: Aug. 11, 1987

[54] CAPILLARY VISCOMETER

[75] Inventors: Horst Huebner, Hochheim; Guenter Tauber; Peter Hofbauer, both of Hofheim am Taunus; Roland Glatzer, Bad Schwalbach; Guenther Beintze, Mainz; Dieter Wagner; Guenter Riege, both of Wiesbaden, all of Fed. Rep. of Germany

[73] Assignee: Schott Gerate GmbH, Fed. Rep. of Germany

[21] Appl. No.: 826,310

[22] Filed: Feb. 5, 1986

[30] Foreign Application Priority Data

Feb. 20, 1985 [DE] Fed. Rep. of Germany ... 8504764[U]

[51] Int. Cl.$^4$ ........................................... G01N 11/06
[52] U.S. Cl. ........................................ 73/55; 73/295; 73/747
[58] Field of Search ................... 73/55, 295, 747, 749; 374/185

[56] References Cited

U.S. PATENT DOCUMENTS

| 3,082,625 | 3/1963 | Zimmerman | 374/185 X |
| 3,153,769 | 10/1964 | Moses | 374/185 X |
| 3,798,960 | 3/1974 | Glass | 73/55 |
| 4,441,358 | 4/1984 | Osborne | 73/55 |

FOREIGN PATENT DOCUMENTS

| 2242172 | 3/1974 | Fed. Rep. of Germany | 73/55 |
| 136654 | 7/1979 | German Democratic Rep. | 73/55 |
| 842484 | 6/1981 | U.S.S.R. | 73/55 |

Primary Examiner—Stewart J. Levy
Assistant Examiner—Joseph W. Roskos
Attorney, Agent, or Firm—Fuller, Puerner & Hohenfeldt

[57] ABSTRACT

A capillary viscometer in which the liquid meniscus is detected by sensing electrical resistance changes in hermetically sealed electrical resistors which are spaced apart at the two levels in the measuring tube in which the meniscus is to be detected. The resistors are encased in glass and the electrical leads to these resistors are passed through glass tubes to a cable connector.

4 Claims, 2 Drawing Figures

CAPILLARY VISCOMETER

BACKGROUND OF THE INVENTION

The invention disclosed herein is a viscometer for measuring the viscosity of liquids, particularly, liquids with Newtonian or approximately Newtonian flow properties.

In capillary viscometers the test liquid is allowed to flow through an outlet tube (measuring tube), which is narrowed into a capillary tube above the outlet. There are two axially spaced apart reference marks in the tube and the space or volume between the two reference marks is precisely known. During measurement of viscosity, the sample liquid is allowed to flow through the measuring tube and the time that it takes for the liquid meniscus to drop from the upper to the lower reference mark is accurately determined. From the measured time, the viscosity of the liquid to be investigated can be calculated with the formula $v = t \cdot K$ where $v$ = kinematic viscosity (mm$^2$ per sec.)
$t$ = measured flow time
$K$ = instrument constant In prior art viscometers two annular reference marks on the measuring tube are used and the flow time of the liquid meniscus between the two marks was measured manually with a stop watch. Numerous other methods for observation or for sensing when the liquid meniscus passes a reference mark have also been suggested and used.

Optical sensing of the reference marks is described by Kirchner, Chem. Eng. Techn. 31, 525 (1959) and Hughes and Rohen, J.Sc. Instr. 2, 12 (1969). Detecting the meniscus at the reference marks using fiber optics has been proposed by Smith, Analyst Ang. 95, 743 (1970) and in the German GM 7 104 411. German Patent No. 832,691 discloses how to sense the meniscus using high voltage sparks. U.S. Pat. No. 3,798,960 describes a capillary viscometer into which resistances are sealed by means of resin, particularly, an epoxy resin, for sensing the meniscus.

Since the majority of liquids are clear or translucent, the meniscus is detected mostly by visual observation or photoelectric sensing. In the category of photoelectric sensing, the method using photoconductive fiber optics has prevailed. This method is used widely in automated viscosity measurement procedures. For liquids with high electrical resistance, the high voltage spark method is usually used as disclosed in German Patent No. 832,691 for measuring the viscosity of mineral oils.

These known methods have one of several disadvantages:

1. All methods employing visual observation are subject to subjective measuring errors by the measuring individual.
2. The photoelectric methods cannot be used with black and/or opaque liquids.
3. The high voltage spark method cannot be used with conductive specimens such as aqueous systems or mineral oils containing some water, or rubbed-off metallic particles or conductive lubricating oil additives.
4. Viscometers having detector elements which are sealed in with organic substances such as resins which are exposed to the sample liquids are not resistant to solvents and/or chemical solutions at the junction point.

The objective of the invention described herein is to provide a viscometer which excludes the possibility of making subjective measurement errors that can determine the viscosity of black and/or opaque liquids that can be used for conductive specimens and, above all, is resistant to any types of chemicals, with the exception of hydrofluoric acid since all surfaces exposed to the test specimen are glass. These objectives are achieved, according to the invention, with a capillary viscometer which is characterized by the fact that glass-encased electrical resistors with positive or negative temperature coefficient are fused hermetically into the viscometer at the location of the usual reference marks.

The principle involved is to mark occurrence of the meniscus by detecting a change in electric resistivity as the meniscus passes a thermally responsive resistive element. Because of the differing thermal conductivity of air and the liquid specimen, the liquid meniscus, generates a sharp change in the measured resistance as the meniscus passes the resistive elements. The concept of detecting a meniscus by detecting the resistivity change in an element such as a thermistor is disclosed in U.S. Pat. No. 3,798,960. However, in that patent the detector elements are in direct contact with the liquid whose viscosity is being measured which means that liquids which might attack the resistive elements must be excluded from making viscosity measurements with the patented viscometer.

The invention is illustrated herein in greater detail in a viscometer of the Ubbelohde type. Viscometers of this type are described in more details in German Patent No. 673,185 as well as in German Standards DIN 51 562 and U.S. Standard ASTM D 2515.

DESCRIPTION OF THE PREFERRED EMBODIMENT

Figures 1, 2:
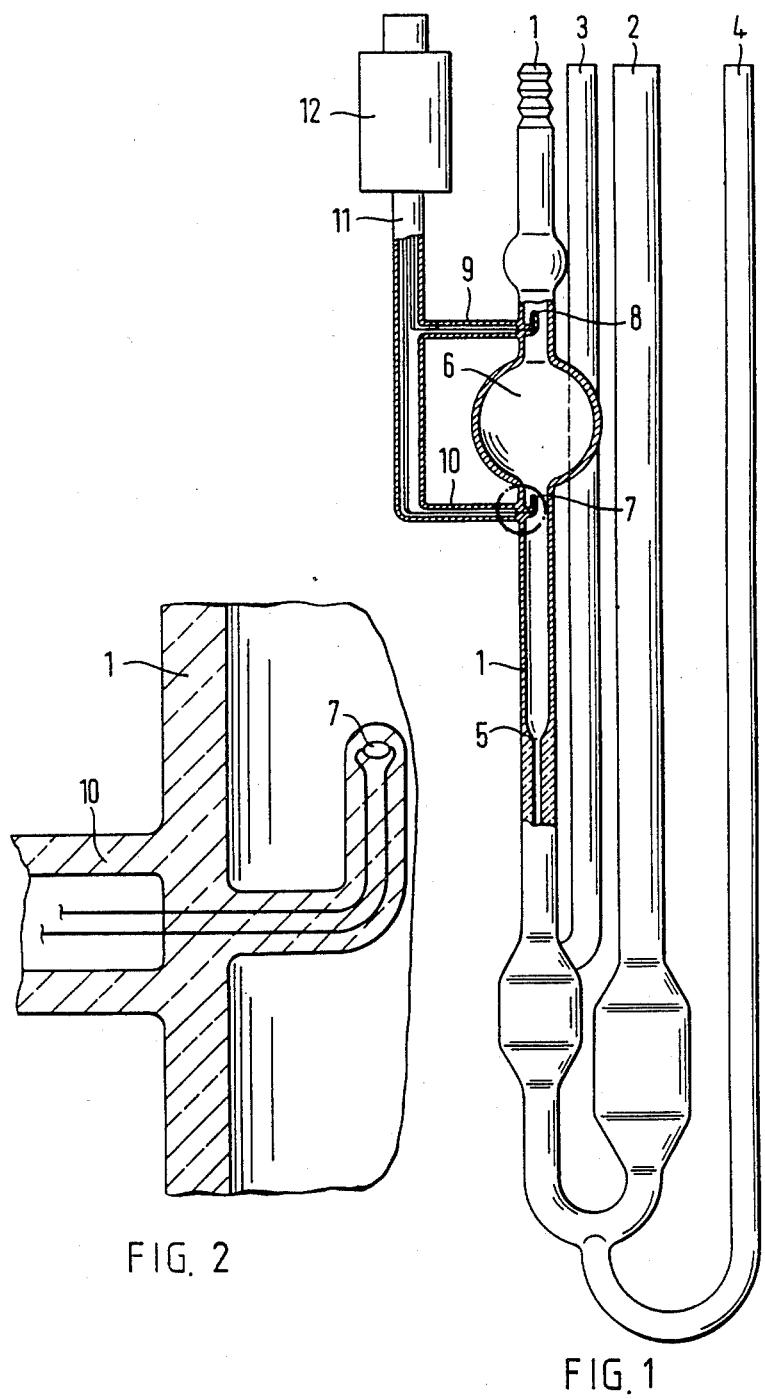
FIG. 1 is an elevation view of a modified viscometer of the Ubbelohde type.
FIG. 2 is a magnified view of that part of the viscometer which is within the dash-dot lined circle in FIG. 1.

FIG. 1 shows a viscometer in which the new measuring elements are incorporated. This viscometer is a modified Ubbelohde type comprising a measuring tube 1, a feed tube 2, a ventilation tube 3 and a flushing tube 4. The measuring tube 1 contains a capillary tube 5 and a measuring bulb 6. Glass-encased negative temperature coefficient resistances 7 and 8 are hermetically fused into a bent glass shape and serve as reference marks in the measuring planes, that is, planes at which the meniscus of the fluid in the measuring tube is to be detected. Elements 7 and 8 are preferably resistors comprised of semi-conductive material such as thermistors. Viscometers such as the depicted viscometer are invariably immersed in a temperature stabilizing liquid bath, not shown. To insulate against outside temperature influence, in particular, to the tempering liquid of the bath, the electric leads leading to the temperature sensors 7 and 8 are directed away laterally in glass tubes 9 and 10 and led upwards in an insulating fashion in a single tube 11. The two pairs of conductors in tube 11 terminate in a moisture proof quadruple pin electrical connection jack 12 which is high enough to extend out of the liquid tempering bath in which the viscometer is immersed. A four conductor cable, not shown, would be plugged into jack 12 when the viscometer is in use. The signals due to the temperature responses of the resistive elements 7 and 8 are conducted to a device, not shown, which is triggered to start measuring time when the meniscus passes resistive sensor 8 and to terminate measuring the time interval when the liquid passes resistive sensor 7.

FIG. 2 shows how typical resistive device 7 is coated with glass so as to be electrically isolated from the sample liquid in the measuring tube 1. However, since the glass coating on the resistive element 7 can be quite thin, the test liquid and sensing elements are in good heat exchange relationship.

The glass-encased sensor elements 7 and 8 which project into the viscometer are either fused in at a right angle to the tube axis as shown or at an acute angle to this axis and constructed either straight or bent to adjust to the particular type of viscometer, so that a complete, smooth flow-off of the measured material in the viscometer is assured.

The viscometer according to the invention offers a multiplicity of significant advantages. Because the detector elements are completely encased in glass and fused hermetically into the viscometer tube, it is possible that specimens to be measured which are very aggressive chemically and have powerful solvent capacity can be measured in the new viscometer, which is not possible with prior art viscometers into which the resistances are sealed in with synthetic resin.

The new viscometer is resistant to all solvents, solutions and chemicals except hydrofluoric acid. It has an advantage over viscometers that depend upon the high voltage spark method for locating the meniscus in that electrically conductive specimens can be measured. This is particularly advantageous with oils or lubricating agents which contain water and/or rubbed off metallic particles and/or conductive additives.

The new viscometer design has the advantage that entirely opaque and/or black liquids can be measured which is not possible in prior viscometers that depend on visual observation or photoelectric sensing to detect the meniscus.

The invention makes it possible for the first time to measure a used mineral oil containing contaminants such as water or metal particles or containing materials that make the mineral oil opaque such as by the presence of the combustion product, carbon. There is no need to replace the sensing elements after a contaminating test fluid has passed through the viscometer. It is only necessary to rinse out the viscometer after a use and proceed with the next measurement with confidence that the response characteristics of the sensing elements have not changed.

Those skilled in the art will recognize that the invention can be applied to capillary viscometers of any type, for example, to the Cannon-Fenske type as described in German standards DIN 51 366 and ASTM D 2515, to viscometers of the Ostwald type and to other flow viscometers as well as the Ubbelohde type which was used to exemplify application of the invention herein.

We claim:

1. A viscometer including a glass tubular member in which there are two levels at which the meniscus of the liquid under test is sensed for determining the viscosity of said liquid, and the improvement comprising temperature sensitive electrical resistive elements and glass fused onto said elements to form a complete hermetic seal about said elements, the glass on said elements being fused onto said glass tubular member to locate said elements, respectively, at said levels inside of said tubular member and with only said fused-on glass exposed in said tubular member.

2. The viscometer according to claim 1 including glass tubes sealed to said tubular member and to said glass that is fused on said elements, and electrically conductive leads extending from said resistive elements into and through said glass tubes.

3. The viscometer according to any one of claims 1 or 2 which is constructed to operate as a Ubbelohde type viscometer.

4. The viscometer according to any one of claims 1 or 2 wherein said electrical resistive elements are transistors.

* * * * *